United States Patent [19]

Grundei

[11] Patent Number: 4,781,721
[45] Date of Patent: Nov. 1, 1988

[54] BONE-GRAFT MATERIAL AND METHOD OF MANUFACTURE

[75] Inventor: Hans Grundei, Lübeck, Fed. Rep. of Germany

[73] Assignee: S+G Implants, Lubeck, Fed. Rep. of Germany

[21] Appl. No.: 864,571

[22] Filed: May 19, 1986

Related U.S. Application Data

[60] Continuation of Ser. No. 558,693, Dec. 6, 1983, abandoned, which is a division of Ser. No. 313,652, Oct. 22, 1981, abandoned.

[30] Foreign Application Priority Data

Feb. 25, 1981 [DE] Fed. Rep. of Germany ....... 3106917

[51] Int. Cl.⁴ .............................. A61F 2/30; B29H 7/20
[52] U.S. Cl. .......................................... 623/16; 264/35
[58] Field of Search ........................ 623/11, 16, 19, 20, 623/21, 22, 23, 24; 164/34, 35, 36; 264/44

[56] References Cited

U.S. PATENT DOCUMENTS

| | | | |
|---|---|---|---|
| 3,587,713 | 10/1974 | Halsey | 264/44 |
| 3,845,181 | 10/1974 | Rauault | 164/35 |
| 3,905,047 | 9/1975 | Long | 623/16 |
| 3,929,971 | 12/1975 | Roy | 3/1.9 X |
| 4,000,525 | 1/1977 | Klawitter et al. | 3/1.9 |
| 4,051,598 | 10/1977 | Sneer | 128/92 G X |
| 4,101,984 | 7/1978 | MacGregor | 3/1 |
| 4,164,424 | 8/1979 | Klug et al. | 164/132 |
| 4,195,366 | 4/1980 | Jarcho et al. | 3/1.9 |
| 4,371,484 | 2/1983 | Inukai et al. | 264/44 |

FOREIGN PATENT DOCUMENTS

| | | | |
|---|---|---|---|
| 2620907 | 11/1977 | Fed. Rep. of Germany | 3/1.9 |
| 4138006 | 10/1979 | Japan | 623/16 |

OTHER PUBLICATIONS

Hassler, et al., "Long Term Implants of Solid Tri Calcium Phosphate", 27th ACEMB, Oct. 6-10, 1979.
Williams, "New Materials", Biomedical Engineering, Jun, 1973.
Unilab, "Unilab Surgibone for Surgical Implants", Hillside, N.J.

Primary Examiner—Richard J. Apley
Assistant Examiner—David J. Isabella
Attorney, Agent, or Firm—Balogh, Osann, Kramer, Dvorak, Genova & Traub

[57] ABSTRACT

This invention relates to bone-graft material or implant and to the method of producing the same, for the replacement of animal and human bones and bone parts. The material or implant comprises a morphologically stable, open-pored or open-celled moulding having a sponge-like structure. The mean width of the pores or cells in the implant is in the range of 0.5 to 1.5 mms. and preferably of 0.8 to 1.0 mm. The implant may be made of metal or plastic material, and may be of any desired shape, such as a wedge, a key, a parallelepiped, a cylinder, a disc or a sheath, for example.

2 Claims, 3 Drawing Sheets

BONE-GRAFT MATERIAL AND METHOD OF MANUFACTURE

This application is a continuation of application Ser. No. 558,693, now abandoned, filed Dec. 6, 1983, which in turn is a divisional of U.S. Ser. No. 313,652, now abandoned, filed Oct. 22, 1981.

BACKGROUND OF THE INVENTION

The present invention relates to bone-graft material intended as a replacement for animal and human bone tissue e.g. whole bones and parts of bones, and also to methods of manufacturing such material.

To avoid transplantation of bones in the case of bone or joint defects and of fractures of the animal or human skeleton, involving extremely protracted organic merging into their osseous seat, it has already been proposed to make use of a reticular structure of stable form as an implant or graft, which is assembled from compatible threads or fibres of plastics material or metal. It has been observed that a reticular structure of this kind merges organically into its osseous seat within a comparatively short time by penetration of bone tissue, but such reticular structures are extremely difficult to produce, especially if it is necessary to obtain the absolutely essential morphological stability and a high carrying capacity, as well as a precise configuration.

It is known moreover that the shanks of hip joint endoprosthesis consisting of metal may be made hollow and that the shank wall may be provided with holes throughout the periphery to allow bone tissue to grow thereinto and fill them. The production of shanks of this kind requires considerable time and labour, apart from the fact that the holes should have a particular mutual spacing to prevent weakening the shank. Bone tissue may moreover grow in only at the points of the spaced-apart wall perforations.

It is also known that shanks of ceramic material intended for joint endoprostheses may be given a roughened external surface to bring about an improved bond with the bone cement applied. A growth of bone tissue into the graft or implant cannot occur in such case.

SUMMARY OF THE INVENTION

It is an object of the invention to provide a bone-graft or implant which is uncomplicated to manufacture, has an extremely stable shape, has the required carrying capacity and allows of immediate in-growth of bone tissue with subsequent bone formation, to secure early organic merging of the graft into its osseous seat.

To achieve this and other objects, the invention consists in bone-graft material for the replacement of animal or human bone tissue, which comprises a morphologically stable, open-pored or open-celled moulding having a sponge-like structure.

Graft or implant material according to the invention may have interconnected pores or cells having a mean width of approximately 0.5 to 1.5 mms, lying advantageously between 0.8 and 1.0 mm. The shape of the implant would be suited to every case encountered, and may for example be formed as a wedge or key, parallelepiped, cylinder, disc or sheath. The materials applied are compatible metals, metal alloys, plastics materials or ceramic materials.

In view of the open-pored or open-celled structure of the implant having a spongy texture, the bone tissue may grow immediately into the interconnected pores or cells with subsequent transformation into bone, that is to say throughout the periphery, so that organic merging into the osseous seat occurs extremely early. An extremely high morphological stability and carrying capacity are obtained by virtue of the material applied, and the application of bone cement may largely be omitted.

The invention also consists in a method of manufacturing such a graft or implant material wherein the open-pored or open-celled cavities of a lost pattern or model corresponding to the positive form of the implant are filled with a moulding material to form a core or negative mould, the core is freed from the pattern material, said cavities of the core or negative mould are filled with the material of the implant, and the resultant solidified implant element is freed of the core material.

Open-pored or open-celled natural sponge, synthetic sponge or spongy animal bone determining the structure of the implant may advantageously be applied as pattern or modelling material, and gypsum, salt, ceramics or an embedding composition may primarily be considered as core or moulding material, for example as used in orthodontic laboratories for the production of false teeth. The core material and the implant material are placed in the lost model or pattern in the liquid or flowing condition by casting, immersion or/and centrifuging, and the pattern material as well as the core material may be removed at will in accordance with the nature of the materials, by the application of heat, e.g. by calcination, by means of solvents, scavenging means, blowing or the like.

According to another method or the manufacture of the graft or implant materials an open-pored or sponge-like structure, a liquid plastics material or a liquid metal alloy is intermixed with an expanding agent in a mould which preferably corresponds to the form of an implant, and is caused to solidify under vacuum if appropriate. In this case too, an implant is produced by means of the expanding agent added, the pre-size of which depends on the nature and quantity of the expanding agent added, e.g. gas-forming aluminium powder, hydrogen peroxide or chloride of lime, provided that the initial material is an appropriate plastics material in liquid form. The manufacturing method is carried out similarly to the manner in which aerated concrete is made, solidification occurring in unexpanded steam, for example. Corresponding appropriate expanding agents, which may be known per se, may also be applied in the case of a metal alloy in liquid form.

In another embodiment, the graft or implant material is made by a process known in powder metallurgy, according to which the material is produced from a powder consisting of a variety of metals utilised for the production of compatible implant alloys. To this end, the powder is compacted, whereupon a hot-consolidation or sintering operation is performed, if appropriate under vacuum, with subsequent cooling, leaving a residual porous structure.

Powder metallurgy processes of this kind are applied for example for the production of capillary metal bearings, filters or the like. The pore size may then be determined by the degree of compaction of the initial metal powder, the sintering temperatures and also by complementary application of expanding agents, the pore size of approximately 0.8 to 1.0 mm being advantageous for the production of the implant. Any residues of the expanding agents or of possible additives remaining in the pores may be removed by physical means, e.g. by heating or blowing out, or by chemical means.

BRIEF DESCRIPTION OF THE DRAWINGS

In order that the invention may be more clearly understood, reference will now be made to the accompanying drawings which show certain embodiments thereof by way of example, and in which.

DETAILED DESCRIPTION OF PREFERRED EMBODIMENTS

Figure 1:
FIG. 1 shows a shank which is to be implanted for the femur section of a knee joint endoprosthesis.

Referring to the drawings, according to FIG. 1, the shank 1 of the femur section of a knee-joint endoprosthesis which is to be inserted into the thigh is illustrated as an open-pored or open-celled implant having a sponge-like structure of the nature specified, and may for example be made from a compatible metal alloy.

Figure 2:
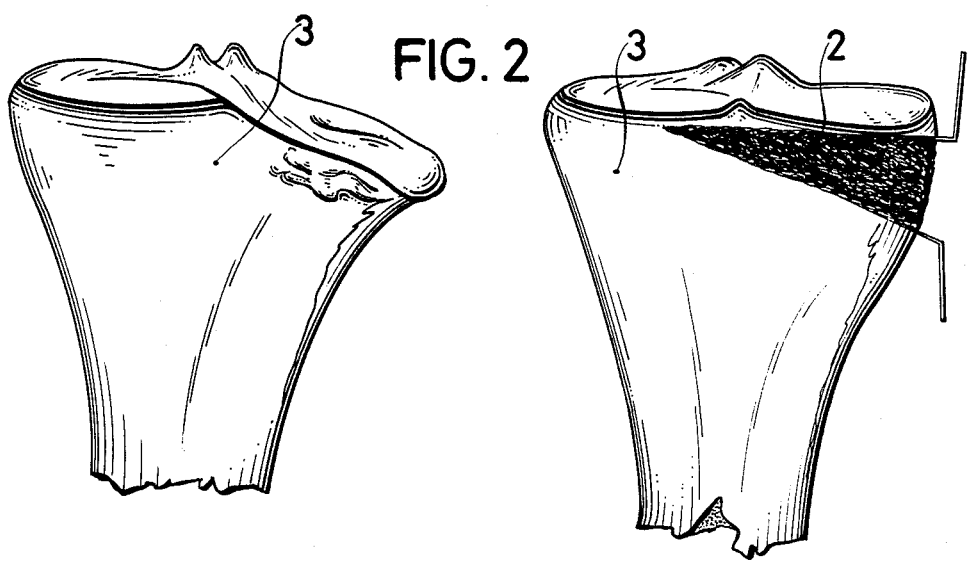
FIG. 2 shows a wedge-shaped implant for elimination of a compressive fracture.

FIG. 2 shows an implant 2 in the form of a wedge, to enable a compressive fracture in the top of the shin bone 3 to be eliminated. This wedge shape may also be applied in the case of compressive fractures in the heel bone or the like.

Figure 3:
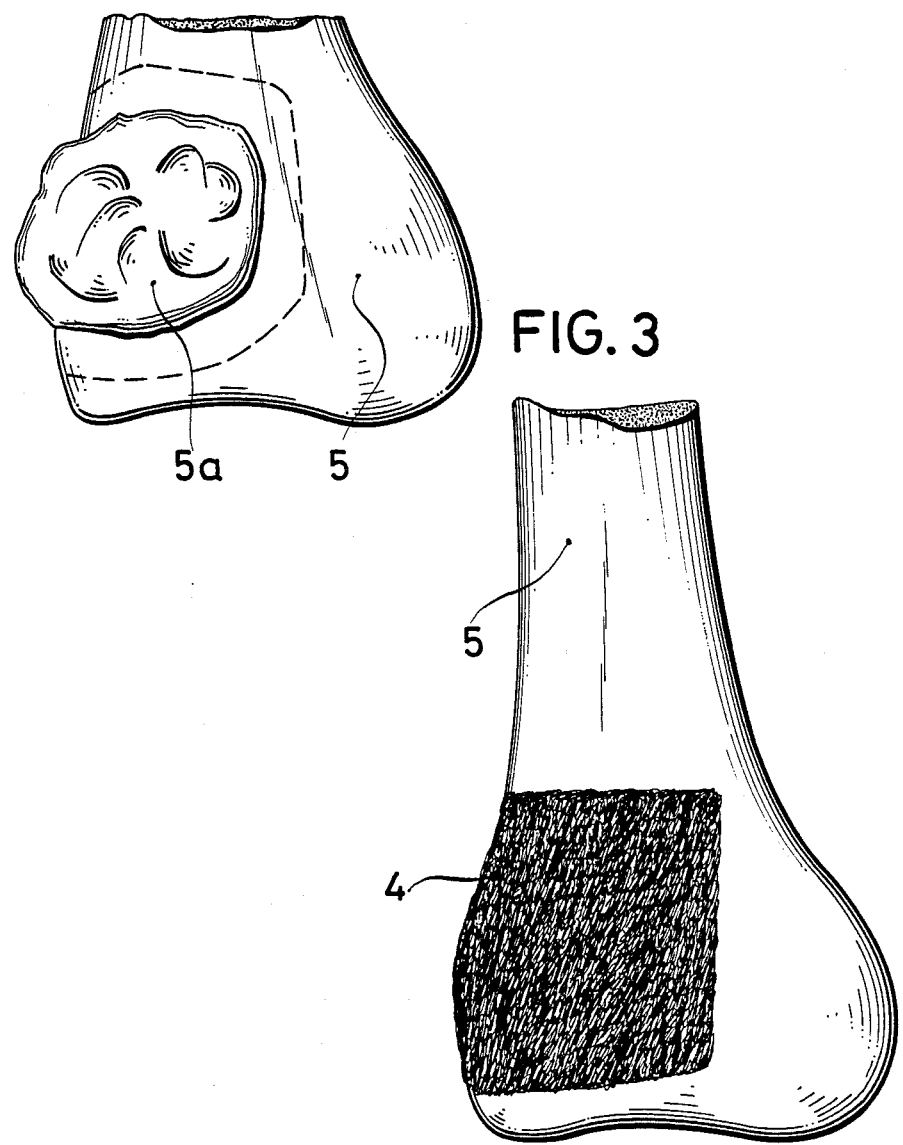
FIG. 3 shows an implant intended as a substitute for a bone section destroyed by a tumour.

According to FIG. 3, the implant 4 has the shape of a bone element, e.g. at the lower extremity of a thigh bone 5, which had been destroyed by a tumour 5a and has been replaced in this case by an implant in accordance with the invention.

Figure 4:
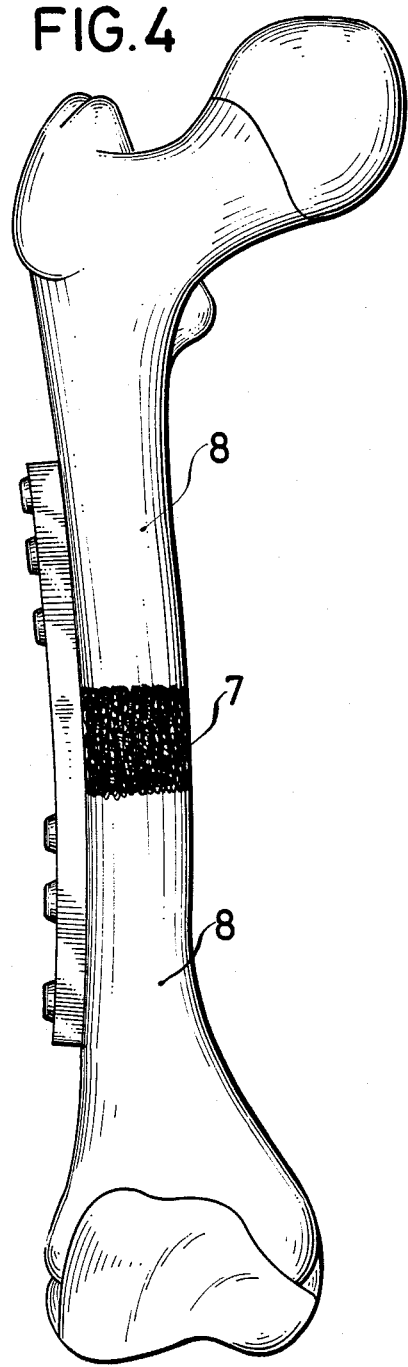
FIG. 4 shows an implant for insertion into a thigh bone after a resection.

The implant 7 according to FIG. 4 has the approximate shape of a cylinder which, after resection of an incorrectly-formed joint of a thigh bone 8, is inserted between the two bone sections which are splinted together during the time in which they are knitting together. The moulding material 7 may be machined or otherwise processed to form the final shape of the implants.

Figure 5:
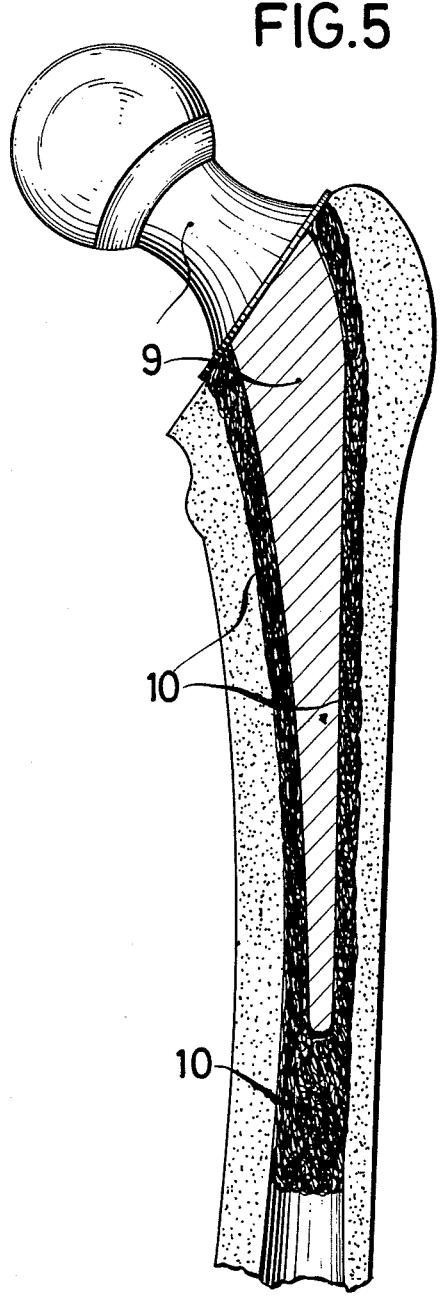
FIG. 5 shows an implant acting as a sheath or scabbard on a shank of a thigh joint endoprosthesis.

FIG. 5 illustrates an endoprosthesis 9 of a hip joint which consists of a compatible metal alloy, plastics or ceramics material. This endoprosthesis 9 is sheathed by a sleeve-like open-pored implant 10 in accordance with the invention.

I claim:

1. A method for manufacturing a morphologically stable implant for replacement of animal or human bone, which implant comprises an open-pored or open-celled porous sponge-like structure of metal having pores or cells of a mean width in the range of 0.5–1.5 mm, method comprising using an open-pored or open-celled sponge as a positive molding pattern for the implant, the sponge pores or cells having a mean width in the range of 0.5–1.5 mm, filling the pores or cells of the sponge with a heat resistant orthodonically embedding material, applying heat to the sponge filled with said embedding material so as to remove the sponge by vaporizing thereof, and wherein said embedding material remains to form a core having cavities or openings corresponding to the sponge, filling the cavities or openings of said core with a metal by casting, and removing said core so as to obtain a metal implant having a sponge-like structure provided with pores or cells corresponding to the pores or cells of the sponge, and having a mean width of 0.5–1.5 mm.

2. A method according to claim 1, for manufacturing a morphologically stable implant, which implant comprises an open-pored, open-celled porous sponge-like structure of a plastic material, wherein the cavities or openings of said core are filled with a plastic material by centrifuging, so as to obtain an implant of plastic material having a sponge-like structure provided with pores or cells corresponding to the pores or cells of the sponge.

* * * * *